United States Patent [19]

Eguchi et al.

[11] 4,414,908
[45] Nov. 15, 1983

[54] SUTURING MACHINE FOR MEDICAL TREATMENT

[75] Inventors: Yasukata Eguchi, Kunitachi; Susumu Hanyu, Hachioji; Reishi Nemoto, Kanagawa; Masayoshi Takahashi, Sagamihara, all of Japan

[73] Assignee: Janome Sewing Machine Co. Ltd., Tokyo, Japan

[21] Appl. No.: 210,764

[22] Filed: Nov. 26, 1980

[30] Foreign Application Priority Data

Dec. 4, 1979 [JP] Japan ................................ 54-156358
May 12, 1980 [JP] Japan ................................ 55-61713

[51] Int. Cl.$^3$ .......................................... D05B 1/02
[52] U.S. Cl. ............................ 112/169; 128/334 R; 112/222
[58] Field of Search .............. 112/169, 185, 194, 195; 128/334 R, 334 C, 339, 326

[56] References Cited

U.S. PATENT DOCUMENTS

| | | | |
|---|---|---|---|
| 1,258,594 | 3/1918 | Miller | 112/169 |
| 2,104,029 | 1/1938 | Eshman | 128/326 |
| 2,479,017 | 8/1949 | Merson et al. | 112/169 |
| 2,507,814 | 5/1950 | Rantanen | 112/169 |
| 2,577,240 | 12/1951 | Findley | 128/325 |
| 3,957,004 | 5/1976 | Ketterer et al. | 112/169 |

*Primary Examiner*—H. Hampton Hunter
*Attorney, Agent, or Firm*—Michael J. Striker

[57] ABSTRACT

A suturing machine for suturing incised parts of a patient by producing continuous stitches by means of a curved needle and a shuttle includes a pair of grips terminated with jaws adapted to hold the curved needle which forms a thread loop on the parts to be sutured. A shuttle holder is slidably positioned on one of the grips to move the shuttle with a shuttle thread towards the curved needle to produce a lock stitch with the thread loop. The shuttle holder functions when the needle is standstill.

5 Claims, 35 Drawing Figures

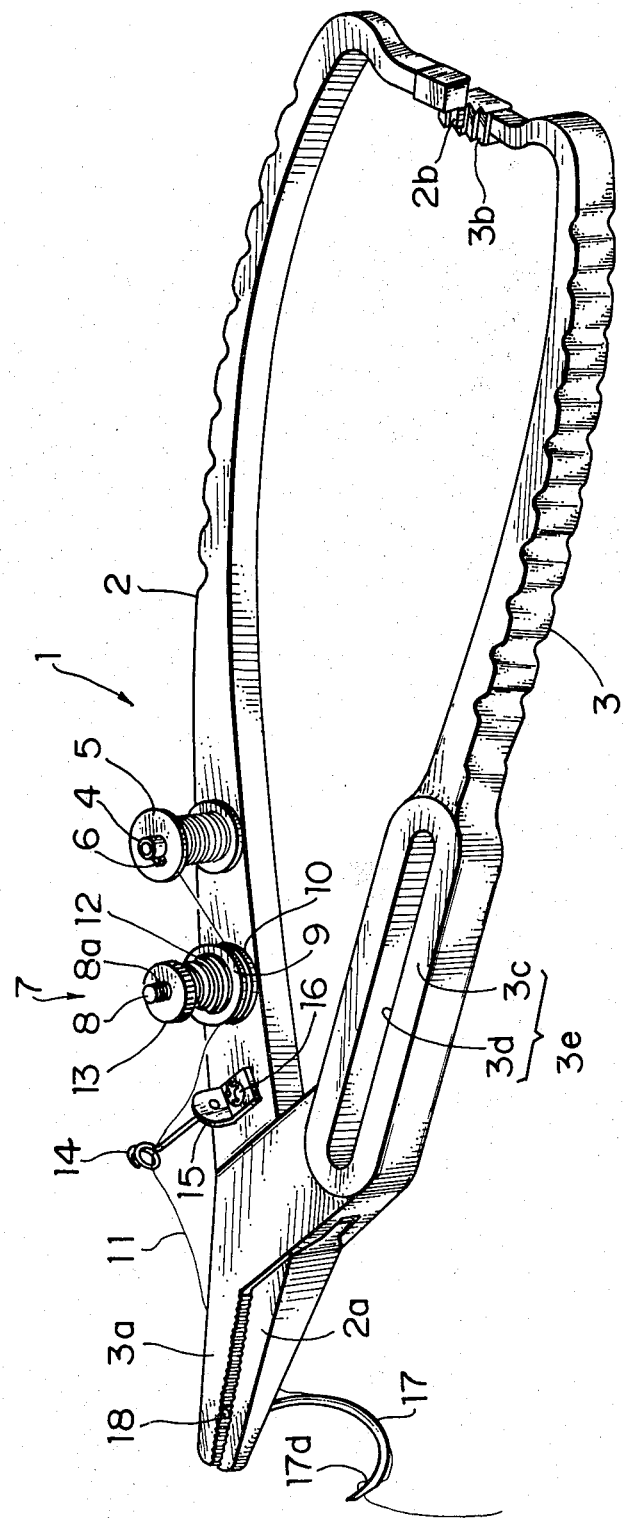

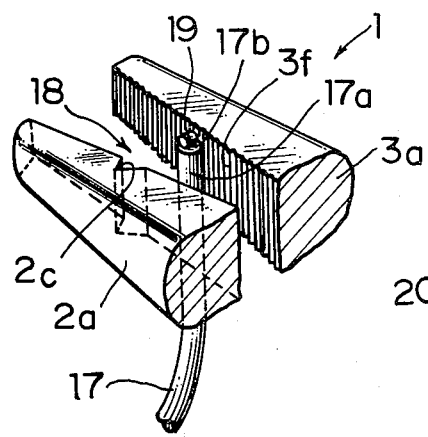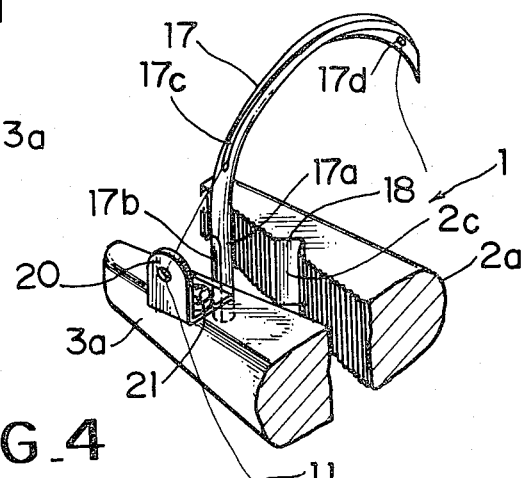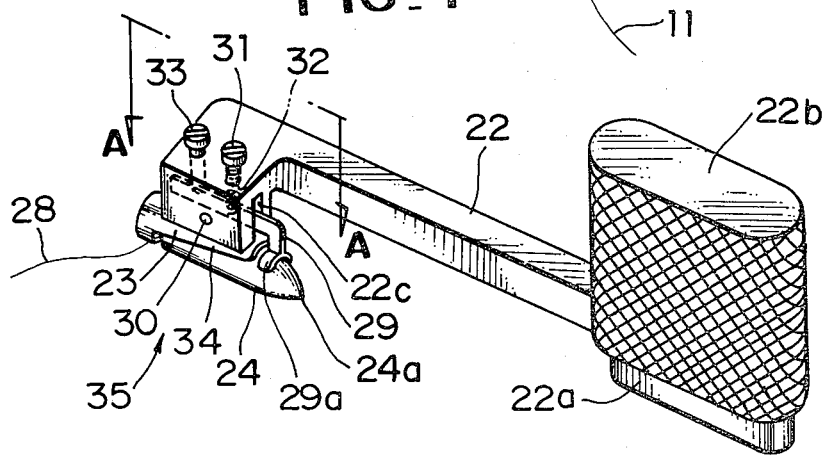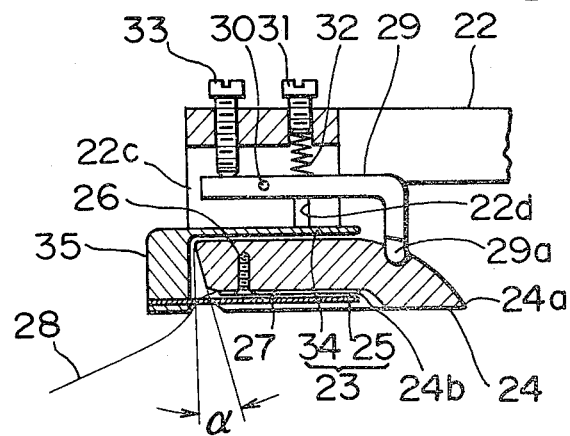

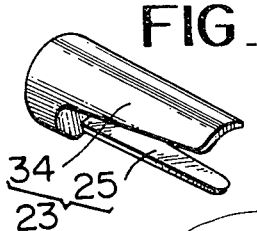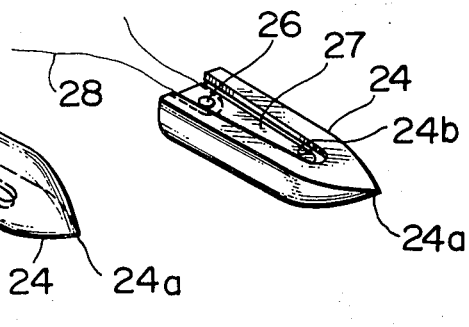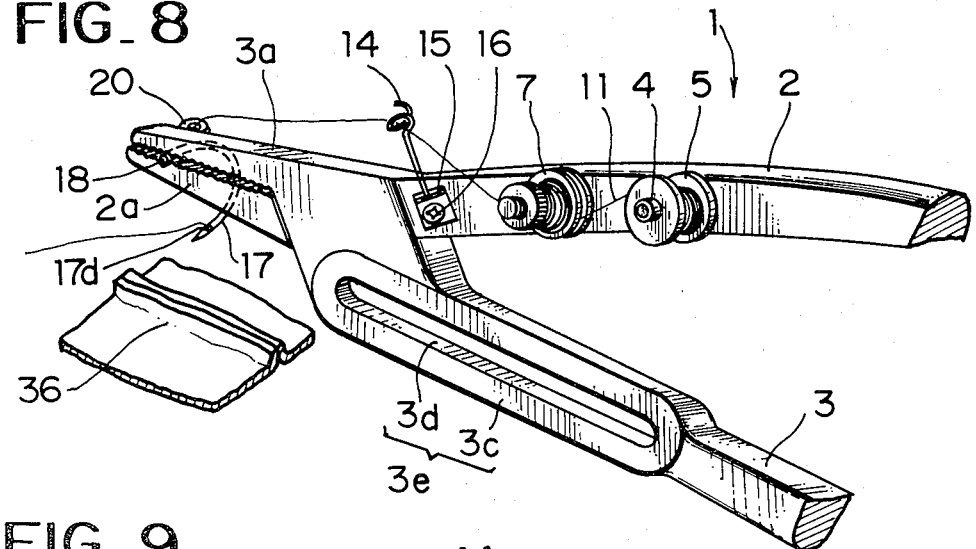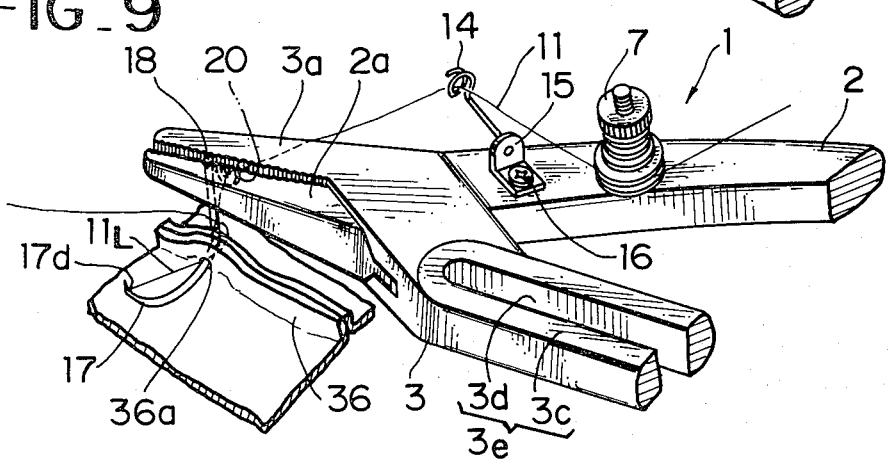

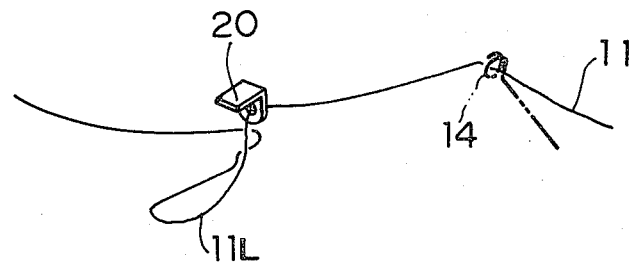
FIG_10
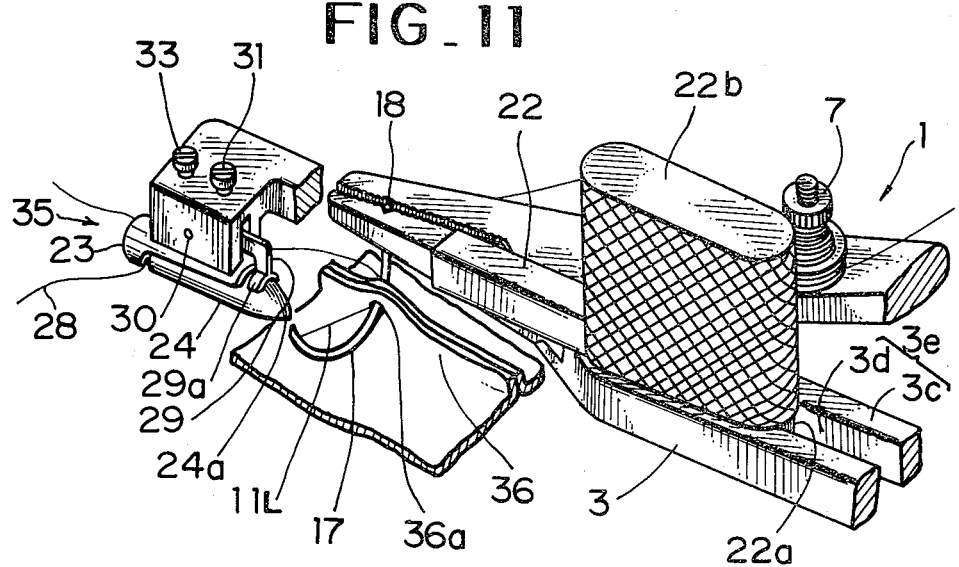
FIG_11
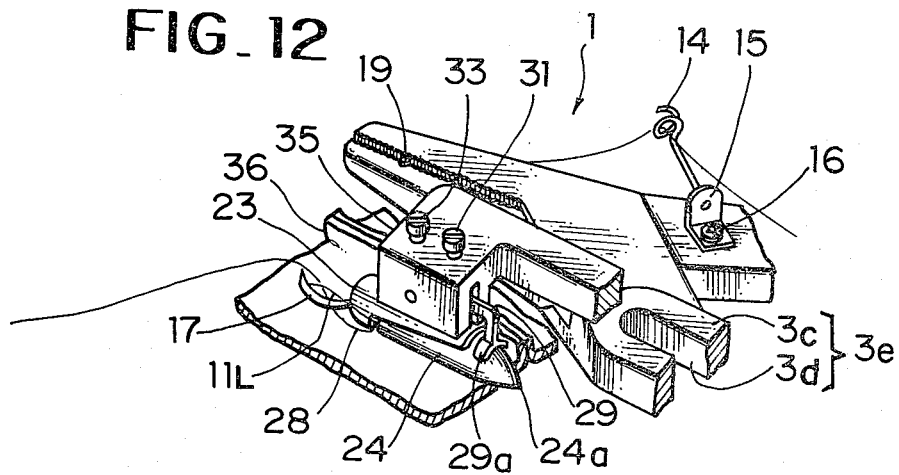
FIG_12

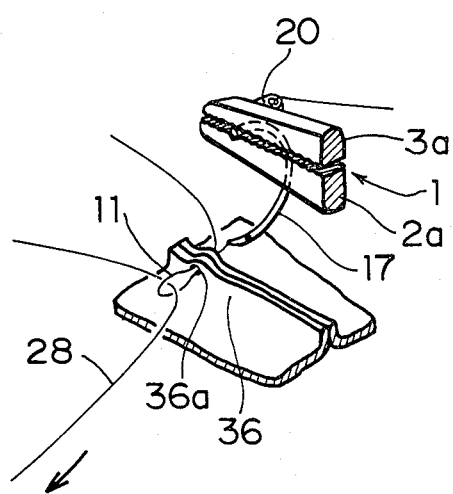
FIG_16
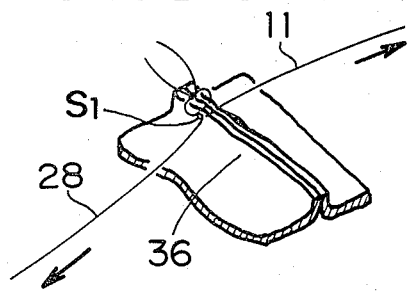
FIG_17
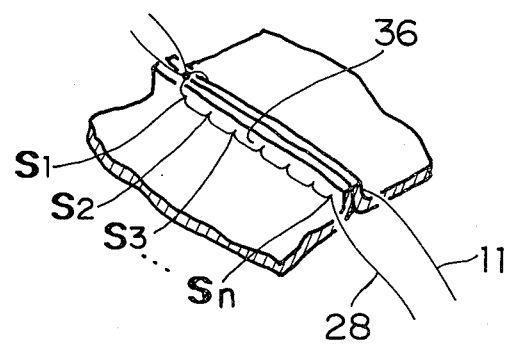
FIG_18
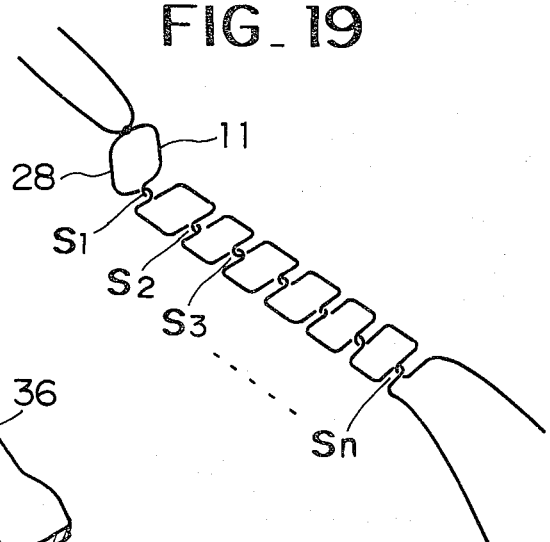
FIG_19

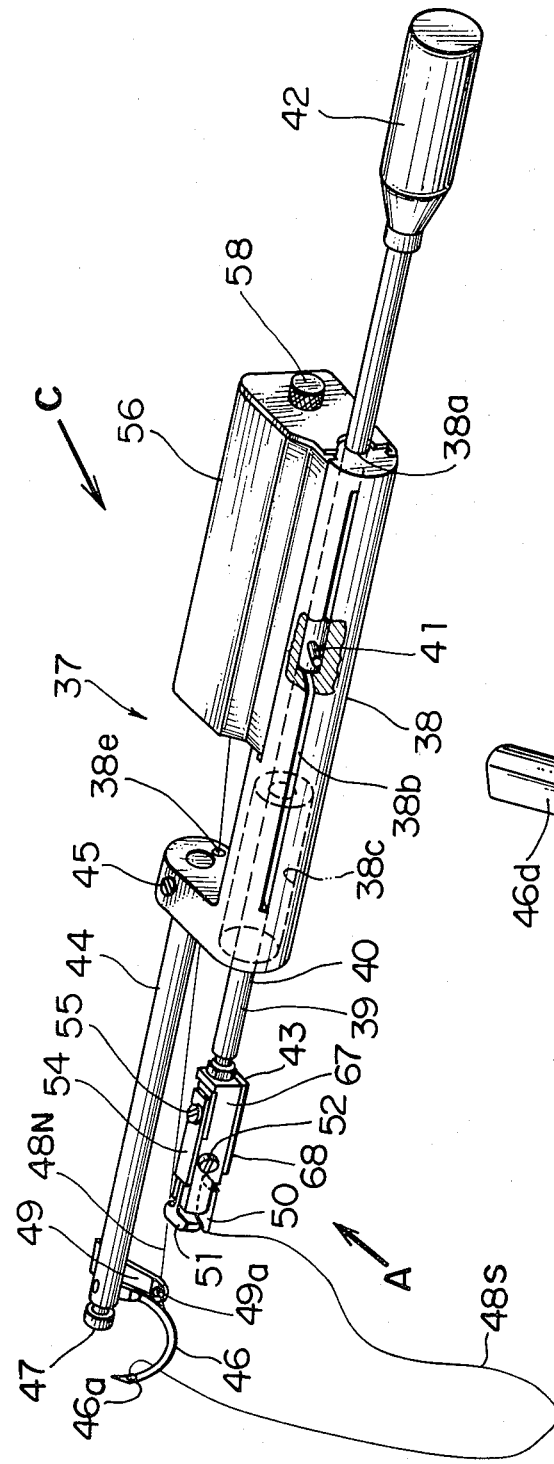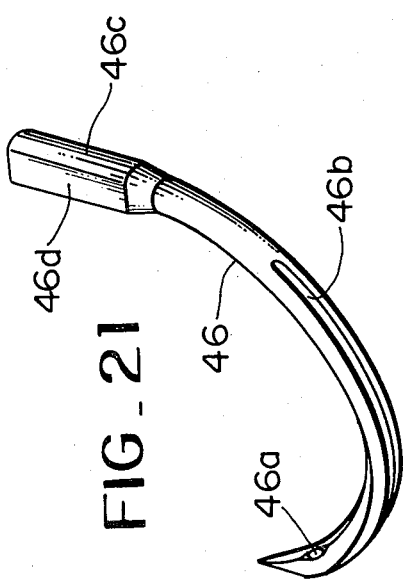

FIG_22
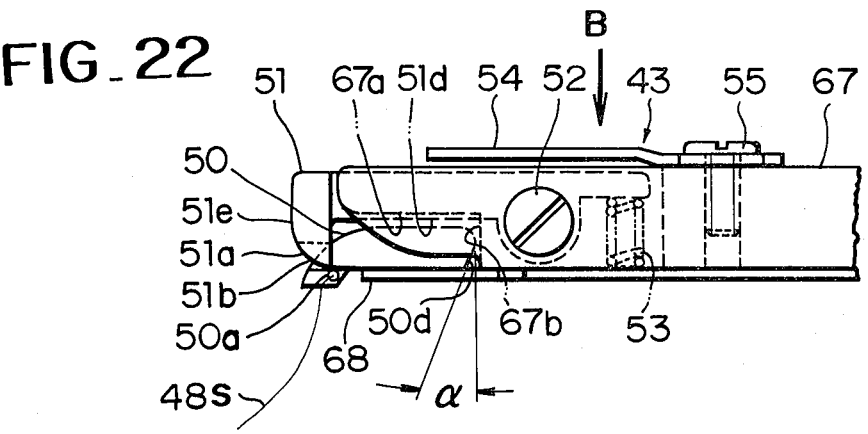
FIG_23
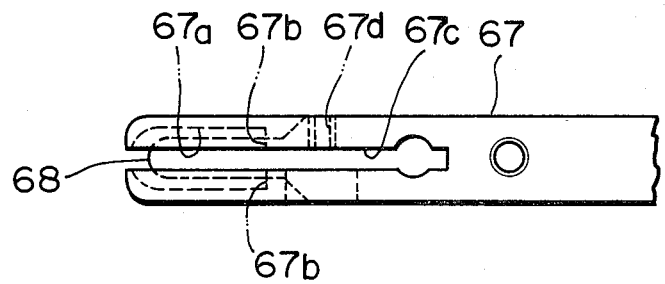
FIG_24
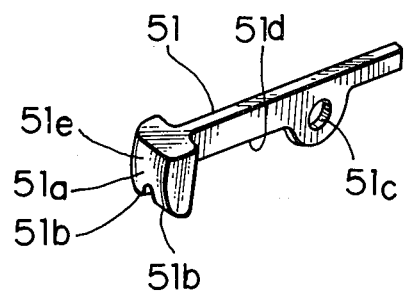
FIG_25
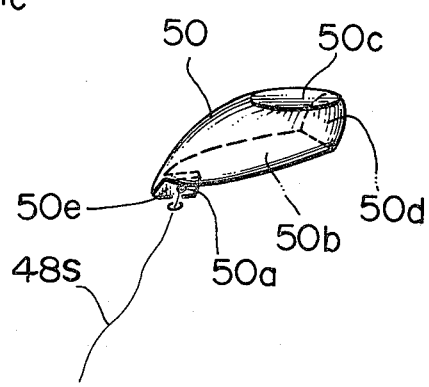

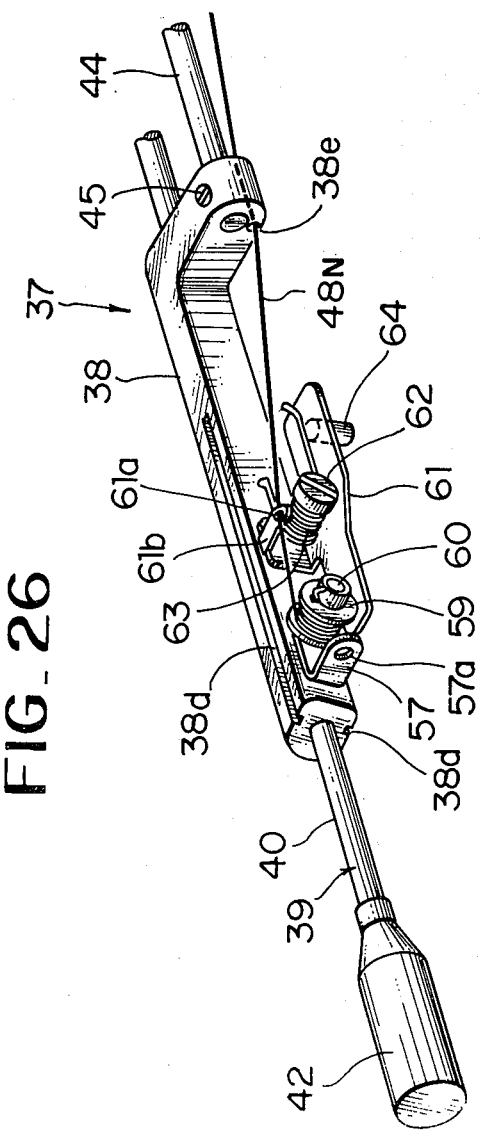
FIG._26
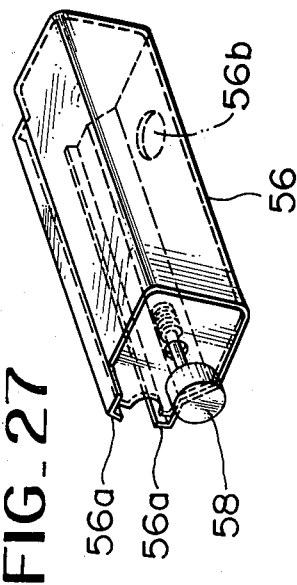
FIG._27

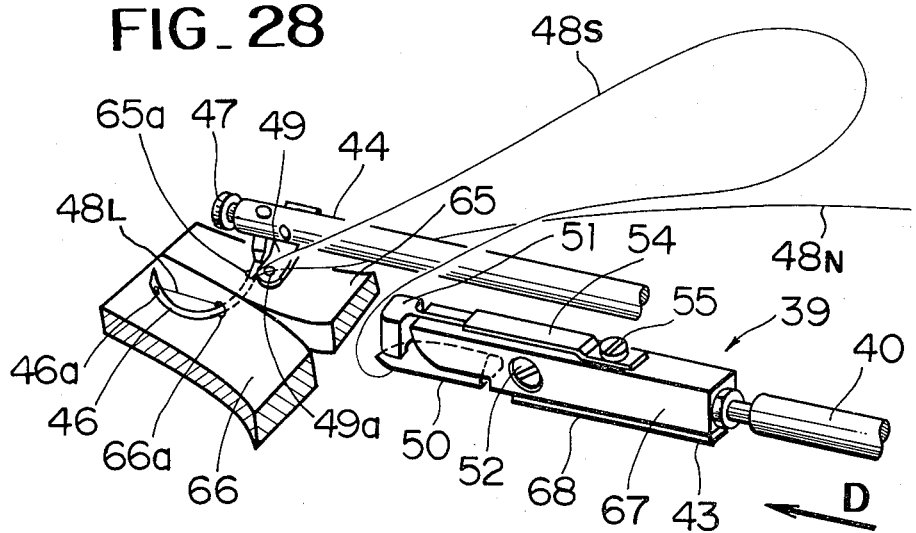
FIG_28
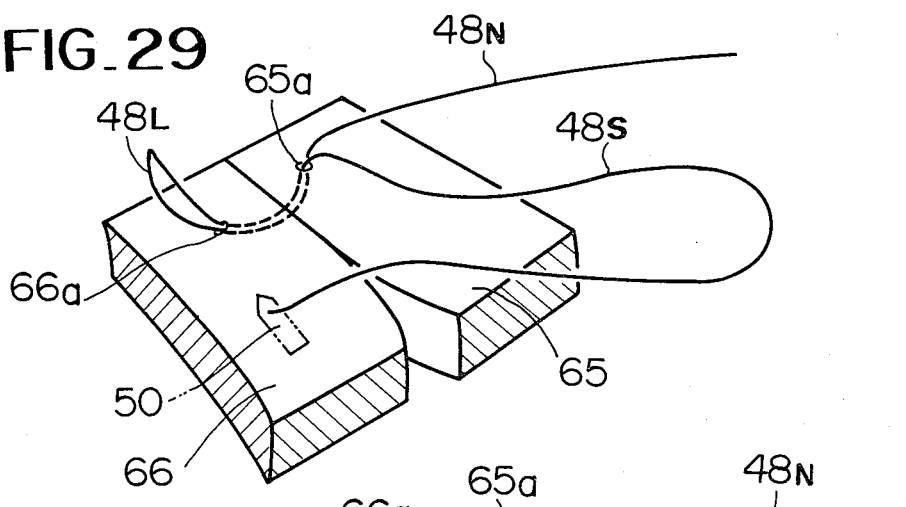
FIG_29
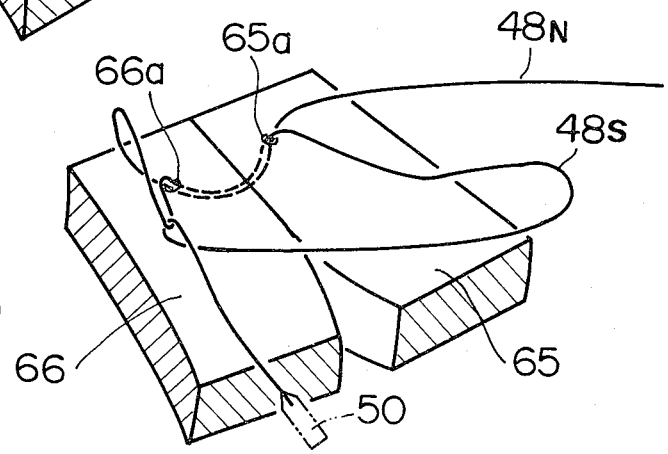
FIG_30

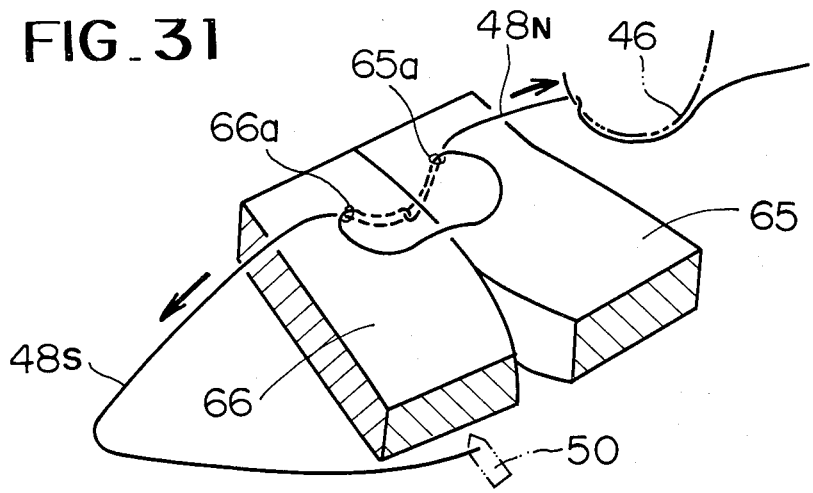
FIG._31
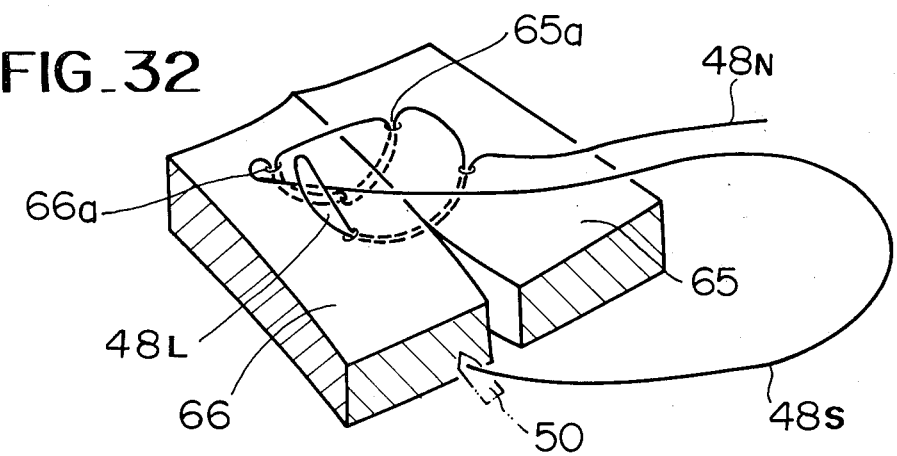
FIG._32
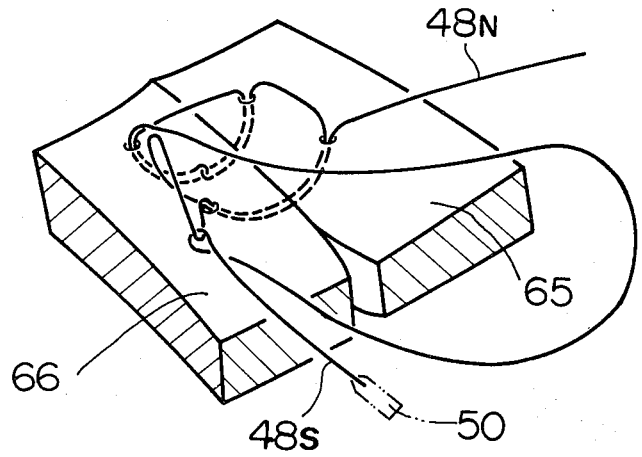
FIG._33

FIG_34
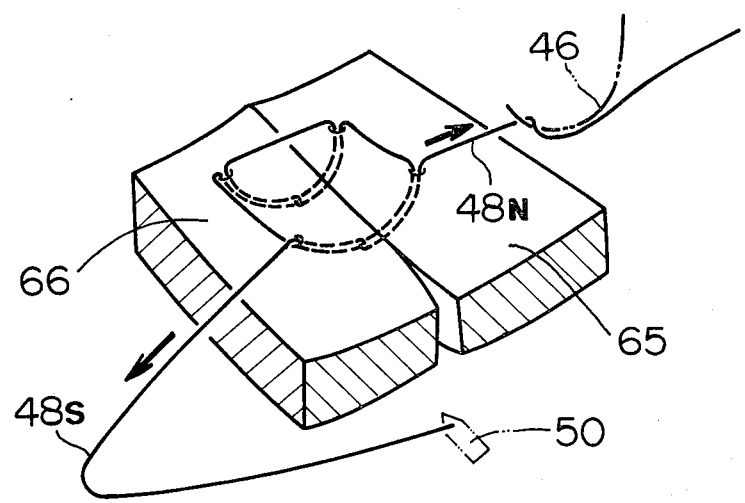
FIG_35
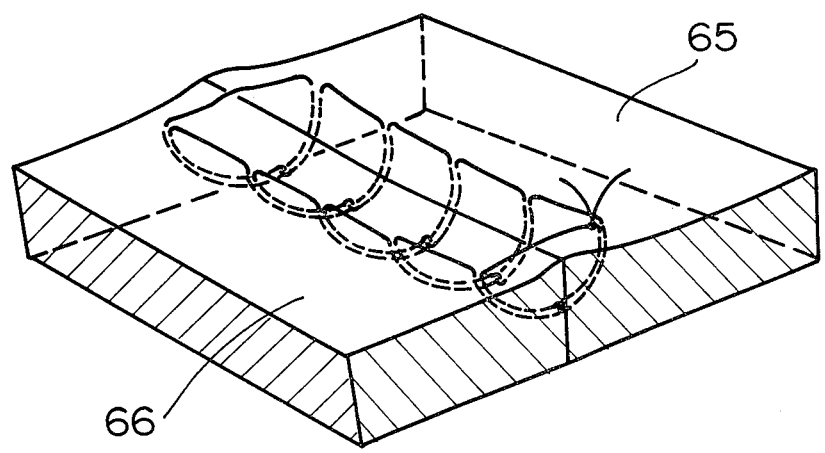

SUTURING MACHINE FOR MEDICAL TREATMENT

BACKGROUND OF THE INVENTION

The invention relates to a suturing machine, and more particularly relates to a suturing machine for medical treatment to suture up the incised parts of the patient continuously by lock stitches with the needle thread and the shuttle thread.

It has been a conventional practice to carry out the suturing operation at the incised parts of the patient by a curved needle formed with a needle eye at the shank thereof, which is held by a holder handled by an operator with a thread passed through the needle eye of the curved needle. Thus the curved needle is inserted→into a part to be sewn up and then the needle is released to manually form up a knotted seam per stitch; therefore the suturing operation has required a long time and a physically heavy burden on the side of the operator as well as the patient.

For shortening the suturing time, there has been provided another machine such as a stapler employing staples made of a metal such as silver. In this case, however, the metal staples remain in the human body, and give an adverse influence to the X-rays which may be taken later to inspect the condition of operated part or other inner organs. Such metal staples will also be obstacles in case the operation is needed again, or may be alien substances which psychologically affect the convalescent.

SUMMARY OF THE INVENTION

The present invention has been provided to eliminate such defects and disadvantages of the prior art. It is a primary object of the invention to provide a suturing machine for medical treatment which is simple in structure and easy in operation to continuously suture up the incised parts of the patient by lock stitches with a needle thread and a shuttle thread.

It is another object of the invention to provide a suturing machine which is effectively and positively operated to suture up a desired part of the patient without injuring the other parts of the patient.

It is still another object of the invention to provide a suturing machine employing silk or nylon threads for making effective the X-rays which may be taken later to inspect the condition of the operated part.

The other objects and advantages of the invention will be apparent from the following description of the preferred embodiments in reference to the attached drawings in reference to the attached drawings.

BRIEF DESCRIPTION OF THE DRAWINGS

FIG. 1 is a perspective view of a needle holder of a suturing machine according to the invention;

FIG. 2 is a perspective view of a holding part of the needle holder and a curved needle;

FIG. 3 is the above mentioned perspective view seen from an opposite direction of FIG. 2;

FIG. 4 is a perspective view of a shuttle holder, of the suturing machine;

FIG. 5 is a cross sectional view taken from the A—A line in FIG. 4;

FIG. 6 is an exploded perspective view of the shuttle holder and a shuttle;

FIG. 7 is a perspective view of the shuttle seen from the arrow B in FIG. 6;

FIGS. 8-19 are views of suturing processes by the suturing machine, wherein

FIG. 8 is a view starting the suturing operation,

FIG. 9 is a view showing the curved needle penetrated into the part to be sutured, FIG. 10 shows a thread condition in FIG. 9, FIG. 11 is a view showing the shuttle holder attached to the needle holder, FIG. 12 is a view showing the shuttle holder operated, FIG. 13 is a relation between the needle thread and the shuttle thread under a condition in FIG. 12, FIG. 14 is a condition to draw out the needle thread from the shuttle holder, FIG. 15 is a condition to have drawn out the needle thread from the shuttle holder, FIG. 16 is a condition drawing out the curved needle from the penetrated hole of the sutured part, FIG. 17 is a stitch made by the needle thread and the shuttle thread at the sutured part, FIG. 18 is stitches formed in succession, FIG. 19 is a relation between the needle thread and the shuttle thread of stitching in FIG. 18;

FIGS. 20-35 show a second embodiment according to the present invention, wherein FIG. 20 is a perspective view of a suturing machine, FIG. 21 is an enlarged perspective view of the curved needle, FIG. 22 is a shuttle holder seen from an arrow A in FIG. 20, FIG. 23 is a shuttle holder seen from an arrow B in FIG. 22, FIG. 24 is a perspective view of a pawl member, FIG. 25 is a perspective view of the shuttle, FIG. 26 is a perspective view of the suturing machine seen from an arrow C in FIG. 20, and partly abbreviated, FIG. 27 is a perspective view of the grip cover of the suturing machine, FIG. 28 is a perspective view showing the curved needle penetrated into a part to be sutured up, FIGS. 29-34 are views showing the suturing processes, FIG. 29 shows a relation between the needle thread and the shuttle thread under a condition in FIG. 28, FIG. 30 shows the shuttle thread crossed by the needle thread, FIG. 31 shows a condition of tightening the needle thread and the shuttle thread, FIG. 32 shows a relation between the needle thread and the shuttle thread at the second penetration of the curved needle, FIG. 33 shows the shuttle thread crossed by the shuttle thread, FIG. 34 shows a condition of tightening the needle thread and the shuttle thread, and FIG. 35 shows a condition that the suturing is completed.

DETAILED DESCRIPTION OF THE INVENTION

Figure 13:
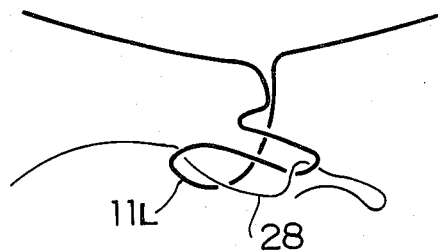

In reference to FIG. 1, a needle holder 1 is substantially composed of a pair of grips 2, 3 each formed with jaws 2a, 3a at one end thereof and abutments 3a, 3b at the other end thereof respectively. The jaws 2a, 3a form a needle holding part 18 of the holder 1. The grips 2, 3 are pivoted to each other so that the needle holding part 18 may be opened and closed by manipulation of the grips 2, 3. The grip 2 is provided with a vertical pin 4 on which a thread wound bobbin 5 is detachably and turnably mounted. The bobbin 5 is provided with a spring 6 which is normally pressed against the pin 4 to prevent the bobbin 5 from being slipped out from the pin 4.

The grip 2 is provided with another vertical pin 8 for mounting thereon a thread tension device 7. As shown, the thread tension device 7 consists of a pair of discs 9, 10 for receiving therebetween the thread 11 of the bobbin 5, a compression spring 12 placed on the discs, and a thumbscrew 13 which is in engagement with a threaded part of the pin 8 to adjust the pressure of the discs 9, 10 through the spring 12. A thread guide 14 is mounted on a base element 15 secured to the grip 2 by a fastening screw 16. The grip 3 has a guide groove 3d formed on the upper face thereof and a flat part 3c provided around the guide groove 3d. As shown in FIG. 3, another thread guide 20 is provided on the rear side of the jaw 3a.

In reference to FIGS. 1, 2 and 3, the needle holding part 18 has a needle positioning notch 2c formed on the inner side of the jaw 2a and has a needle positioning pin 19 secured to an inner indented side 3f of the jaw 3a just opposite to the needle positioning notch 2c, for determining the vertical position of a needle 17. As shown, the needle 17 has an upper straight stem 17a and a curved shank with a needle eye 17d formed at a part adjacent to the painted end. The curved needle 17 has a flat part 17b provided on one side of the stem 17a and a thread guide groove 17c formed on one side of the curved shank and extending therealong. In order to hold the needle 17 with the holder 1, the needle holding part 18 of the holder 1 is opened by manipulation of the grips 2, 3, and the upper end of the stem 17a of the needle 17 is pressed against the positioning pin 19 of the jaw 3a of the holder 1 and the flat face 17b of the stem 17a is pressed against the indented face 17f of the jaw 3a as shown in FIG. 2. Then if the needle holding part 18 is closed, the positioning notch 2c of the jaw 2a engages the stem 17a of the needle 17 and presses the latter against the indented face 17f of the jaw 3a. Thus the needle 17 is vertically positioned by the pin 19 and laterally positioned by the notch 2c, and fixedly held by the holder 1.

In reference to FIG. 4, a shuttle holder 22 is substantially an elongated support having an operating part 22b provided at one end thereof and a base 22a provided on the lower end of the operating part 22b, which is to be received into the guide groove 3d of the needle holder 1. The shuttle holder 22 has a shuttle holding member 23 secured to the other end thereof. As shown in FIG. 6, the shuttle holding member 23 is substantially composed of upper and lower holding tongues 34, 25 each laterally extending and vertically spaced from each other. A shuttle 24 is an elongated member which is as shown semi-circular at the cross section thereof and has a flat bottom and a tapered end 24a. The shuttle 24 has also a recess 24b formed at the bottom thereof for receiving therein the lower holding part 25 of the shuttle holder 23. As shown in FIG. 7, a leaf spring 27 is secured to the recessed bottom 24b by a disc screw 26, so that a shuttle thread 28 may be inserted into between the leaf spring 27 and the recessed bottom 24b. For the convenience sake of thread drawing, which will be mentioned later, the head of the disc screw 26 is positioned in the same plane with the outer face of the leaf spring 27 or is in a plane inner than the outer face of the leaf spring 27, and the rear face of the shuttle 24 is inclined in the rightward direction defining the angle α of about 15° with respect to the vertical plane as shown in FIG. 5.

As shown in FIGS. 4 and 5, the shuttle holder 22 is at the leftward end thereof formed with a vertical slot 22c which is opened at the bottom thereof. An elongated holder element 29 with a depending forked part 29a is turnably arranged in the slot 22c on a pivot pin 30. The clockwise turning movement of the holder element 29 is limited by a vertically threaded adjustable screw 33. Another adjustable screw 31 is employed to press the forked part 29a against the forward end part of the shuttle 24 by way of a compression spring 32 which is guided in a vertical groove 22d formed in the inner faces of walls defining the slot 22c. Thus the holder member 23 and holder element 29 constitute a structure 35 for holding the shuttle 24 in such a manner that the shuttle 24 is laterally adjustable with respect to the holder member 23. The shuttle holding structure provides a clearance between the shuttle 24 and the lower and upper tongues 25, 34 and between the shuttle 24 and the forked part 29a to allow the needle thread to pass through the clearance.

Operation is as follows; Prior to the suturing operation, the shuttle thread 28 is inserted between the recessed bottom 24b of the shuttle 24 and the leaf spring 27 as shown in FIG. 7, and then the shuttle 24 is mounted to the holding structure 35 of the shuttle holder 22. Then the bobbin carrying the needle thread 11 is mounted on the needle holder 1, and the thread 11 is inserted into the thread tension device 7 and passed through the thread guides 14, 20 and is placed in the guide groove 17c of the curved needle 17, and then passed through the needle eye 17d. A part to be sutured up is fixed by a pincette or other suitable instruments as shown in FIG. 8. The needle holder 1 holding the curved needle 17 is inclined as shown in FIG. 8 to penetrate the part 36 to be sutured up. When the curved needle 17 penetrates the part 36, the thread 11L is tensioned between the needle eye 17d and the needle penetrated point 36a as shown in FIG. 9, thus forming a crescent thread loop together with the thread guided in the guide groove 17c of the curved needle 17 (FIG. 10). In this case, it is improper to form a thread loop by utilizing the friction between the thread and the sutured part which is produced when the needle returns as is seen in the ordinary sewing machines, because the thread loop is deformed due to the adhesive blood and becomes difficult to be caught by the shuttle 24.

Then the shuttle holder 22 is mounted on the needle holder 1. Namely as shown in FIG. 11, the base 22a of the operating part 22b of the shuttle holder 22 is inserted into the guide groove 3d of the needle holder 1. Then if the shuttle holder 22 is moved in the rightward direction, the shuttle 24 comes into the loop 11L, and the loop 11L is enlarged as shown in FIG. 12. As a result, the loop 11L comes to the rear end of the shuttle through the clearance between the upper face of the shuttle 24 and the forked part 29a of the holder element 29 and between the upper face of the shuttle and the upper tongue 34 of the holder member 23. The relation between the loop 11L and the shuttle thread 28 is such as shown in FIG. 13.

Figure 14:
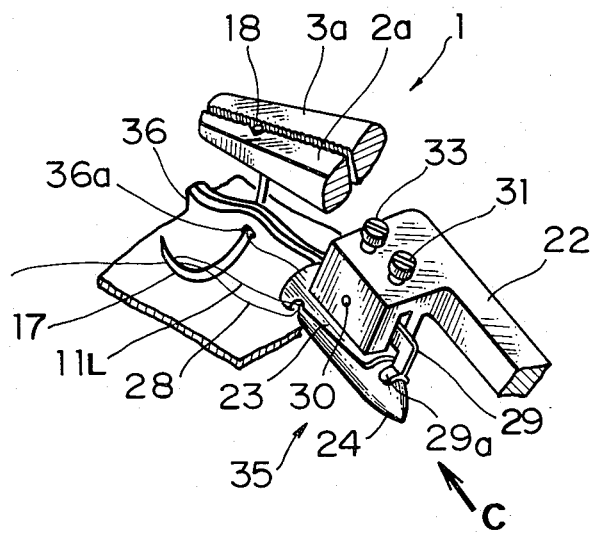
Figure 15:
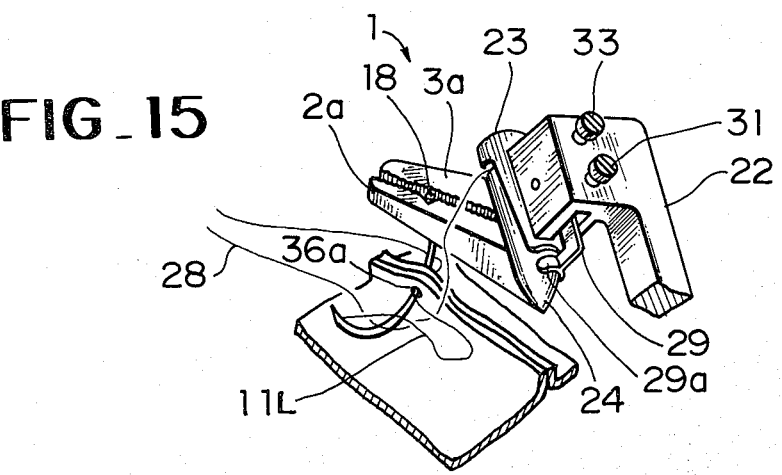

Then the shuttle holder 22 is removed from the needle holder 1, and is inclined in such a manner that the rearward end of the shuttle 24 is slightly lifted up as shown in FIG. 14. In this condition, if the shuttle holder 22 is moved back in the direction indicated by an arrow mark C, the loop 11L is drawn out from the shuttle 24 and shuttle holder structure 35 through the clearance between the leaf spring 27 of shuttle 24 and the lower tongue 25 of the holder member 23. The relation between the loop 11L and the shuttle thread 28 is such as shown in FIG. 15. Thus the loop 11L and the shuttle thread 28 are interlocked to each other, if the curved needle 17 is withdrawn from the penetrated point 36a of the sutured part 36 as shown in FIG. 16. In this condition, the shuttle thread 28 and the needle thread 11 are knotted on the free end side thereof, and then the shuttle holder 22 and the needle holder 1 are pulled in the opposite directions to tighten the threads 11, 28, thereby to form a lock stitch $S_1$ as shown in FIG. 17. In this way, the same stitches $S_2$, $S_3$... Sn are produced repeatedly as shown in FIGS. 18 and 19 and the threads 11, 28 are knotted again at the end of last stitch. Thus the suturing operation is completed.

According to the invention, it is proper to make the suturing operation with the shuttle thread 28 constantly kept about 40 cm–50 cm long from the part to be sutured up. If the shuttle thread 28 is used up, the shuttle 24 is replaced by a new shuttle which is supplied with a new thread to continue the suturing operation.

Now another embodiment of the invention will be explained. In reference to FIG. 20, the suturing machine 37 comprises an L-shaped body 38 which is formed with a bore 38a lengthwise thereof. A rod 40 inserted into the bore 38a has an operating part 42 secured to one end thereof and a shuttle holder 43 secured to the other end thereof. A pin 41 is secured to the intermediate part of the rod 40. The pin 41 is in engagement with a guide groove 38b which is formed in the bore 38a lengthwise thereof. Thus the rod 40 is reciprocated in the bore 38a while it is prevented from turning movement. The shuttle holder 43 is housed in an enlarged bore 38c of the body 38, which is coaxial with the bore 38a, when the rod 40 is moved to the rightward direction to the maximum extent.

As shown, a needle bar 44 is at one end thereof secured to the L-shaped body 38 by a fastening screw 45 in parallel to the rod 40. The needle bar 44 has a curved needle 46 secured to the free end thereof by a fastening screw 47. The curved needle 46 shown in FIG. 21 is substantially same in structure with the needle of the first embodiment, and therefore the description of the needle 46 is omitted here.

In reference to FIGS. 22 and 23, the shuttle holder 43 is substantially a U-shaped frame 67 opened at the bottom which is, however, covered with a shuttle support plate 68. The U-shaped frame 67 forms a chamber 67a together with the bottom support plate 68 for housing a shuttle 50. As shown, the chamber 67a is provided with a pair of spaced abutments for limiting the rightward movement of the shuttle 50. The U-shaped frame 67 has a slot 67c formed in the upper wall lengthwise thereof. A stopper plate 54 is at one end thereof secured to the upper wall of the frame 67 by a fastening screw 55, and is extended over the slot 67c.

FIG. 24 shows a shuttle holding member 51 which is formed with an elongated shank 51d, a mounting hole 51c provided at the intermediate part of the shank 51d and a pawl 51e provided at one end of the shank 51d. The pawl 51e is forked at the lower end thereof to form shuttle holding parts 51b, 51b. The front face 51a of the pawl 51e is smoothed and inclined toward the shuttle holding parts 51b, 51b as shown. The shuttle holding member 51 is turnably mounted in the U-shaped frame 67 by a stepped screw 52 which is inserted into the side wall of the frame 67 and into the hole 51c of the shuttle holding member 51 and threaded into a threaded hole 67a which is formed with the opposite side wall of the frame 67 as shown in FIG. 22. The shuttle holding member 51 is normally biased in the counterclockwise direction by a spring 53 acting on one end of the holding member 51.

FIG. 25 shows a shuttle 50 which is streamlined and pointed at the forward end thereof and inclined at the rear end 50d with an angle about 10° with respect to the vertical plane. The shuttle 50 has a flat bottom 50b and a flat top 50c, and has a vertically projected part 50e formed on the flat bottom 50b at the forward end thereof. The projected part 50e is provided with an eye at which one end of a shuttle thread 48S is knotted. The shuttle is placed in the chamber 67a of the frame 67 as shown in FIG. 22 and is held there by the holding member 51, the forked pawl 51e of which being pressed against the forward end part of the shuttle 50.

In reference to FIG. 26 a thread wound bobbin 59 is mounted on a pin 60 which is secured to one side of the L-shaped frame 38. A brake plate 61 is turnably mounted on the side of the frame 38 by a pivot screw 62. The brake plate 61 is normally biased in the counterclockwise direction by a spring 63 mounted on the pivot screw 62, and is pressed against the side of the bobbin 59 to prevent the bobbin 59 from being freely rotated. The brake plate 61 is provided with an operating projection 64 on the underside thereof. A pair of grooves 38d are provided opposite to each other on the upper and lower faces of the L-shaped frame 38.

FIG. 27 shows a box like cover 56 which is open at one side thereof and has a pair of guide rails 56a each provided oppositely on the opened side thereof. The guide rails 56a are each engaged into the grooves 38d of the frame 38. Thus the cover box 56 is detachably attached to the L-shaped frame to cover the bobbin 59 and the brake plate 61, and is secured to the frame 38 by a fastening screw 58 which is threaded into a threaded hole 57a of a plate element 57 which is fixedly mounted on the frame 38. In this case, the operating projection 64 of the brake plate 61 is extended out of the cover box 56 through an opening provided in the lower side of the cover box 56. The cover box 56 is also used as a grip when the suturing device is operated.

As shown in FIG. 26, a thread guide hole 61a is provided at a bent end 61b of the brake plate 61, another thread guide hole 38e is provided at the rightward end of the L-shaped frame 38, and still another thread guide 49 with a hole 49a is provided at the free end part of the needle bar 44 in the neighbourhood of the needle 46 as shown in FIG. 20.

Operation is as follows; Prior to the suturing operation, the cover box 56 is removed from the L-shaped frame 38, and the bobbin 59 carrying the thread 48N is mounted on the support pin 60. Then the thread 48N is drawn out from the bobbin 59 and is passed through the hole 61a of the thread guide 61 and through the hole 38e of the L-shape frame 38, and then the cover box 56 is attached again to the frame 38. The thread 48N is further passed through the hole 49a of the thread guide 49 and then is passed through the needle eye 46a of the curved needle 46 guided in the curved groove 46b thereof.

Then the screw 55 (FIG. 22) is loosened to displace the stopper plate 54 from the slot 67c of the U-shaped frame 67, and the shuttle holding member 51 is turned in the clockwise direction, and then the shuttle 50 is placed in the chamber 67a, so that the shuttle may be held there by the holding member 51. Then the thread 48N, which is finally passed through the needle eye 46a is knotted to the thread eye 50a of the shuttle 50. This thread is to be called a shuttle thread 48S. As this, if the needle thread 48N and the shuttle thread 48S are continuous, these threads are not needed to be knotted at the initial stitch.

Prior to suturing operation, the shuttle holder 43 is displaced into the enlarged bore 38c of the L-shaped frame 38 by moving the rod 39 in the rightward direction, so that the shuttle holder 43 may not hinder the penetration of the curved needle 46 into the part to be sutured up. At the same time, the drawn out shuttle thread 48S is to be held in a direction spaced from the needle penetrating position by the operator or his assistant.

In this condition, the operator holds the suturing machine at the grip 56 and inserts the curved needle 46 into the sutured parts 65, 66 which are to be fixed by a pincette or other instruments as shown in FIG. 28. Then the needle thread 48N is tensioned between the needle eye 46a and a point 66a of the sutured part 66, and a crescent loop 48L is formed together with the thread guided in the needle groove 46b (in FIG. 21) in the same manner as in the first embodiment. The operating part 42 is then operated to displace the shuttle holder 43 toward the loop 48L in the direction as indicated by an arrow mark D, so that the streamlined shuttle 50 may be inserted into the loop 48L. Then the loop 48L is guided on the upper face of the shuttle 50, passing between the shuttle and the forked pawl 51 and between the rear face 50d of the shuttle 50 and the abutments 67b, 67b of the chamber 67a, to the inclined rear face 50d of the shuttle 50 as is understood from FIG. 22.

The operating part 42 is then operated to return the shuttle holder 43 toward the L-shaped frame 38. The loop 48L is, therefore, guided between the bottom face 50b of the shuttle 50 and the support plate 68 of the chamber 67a and is drawn out from the shuttle 50. Thus the needle thread 48N and the shuttle thread 48S are interlocked to each other. FIG. 29 shows the relation between the threads 48N, 48S before the shuttle 50 is inserted into the loop 48L, and FIG. 30 shows the relation between the threads 48N, 48S after the shuttle has been inserted into the loop 48L and returned toward the L-shaped frame 38.

Then the curved needle 46 is withdrawn from the sutured parts 65, 66, and the needle thread 48N and the shuttle thread 48S are pulled in the opposite directions as shown in FIG. 31. Thus these threads are tightened to form a stitch. In this manner, the same stitches are formed one after another as shown in FIG. 35. FIGS. 32, 33 and 34 show the processes of forming the next stitch by the suturing machine.

It will be understood that each of the elements described above, or two or more together, may also find a useful application in other types of suturing machine differing from the types described above.

While the invention has been illustrated and described as embodied in a suturing machine, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims.

1. A suturing machine for use in medical treatment by producing continuous stitches on parts to be sutured, comprising a curved needle for holding a needle thread; means for holding said needle and operative for inserting said curved needle into the parts to be sutured to form a thread loop; a shuttle for holding a shuttle thread; means for holding said shuttle and operative for inserting the shuttle thread into said thread loop to thereby interlock said loop and to produce a lock stitch, said shuttle holding means being mounted on said needle holding means and being operative when said needle holding means is inoperative with said needle in the raised position, said needle holding means including a pair of grips each having an end portion, the end portions forming jaws operative for releasably holding said curved needle, one of said grips being formed with a guide groove, said shuttle holding means including an elongated support having a shuttle holder at one end thereof, displaceable lengthwise of said one grip and a guiding member at its other end; said guiding member being slidably positioned within said guiding groove for guiding said shuttle holder in its displacement lengthwise of said one grip towards and from the thread loop formed by said curved needle.

2. The suturing machine of claim 1, wherein one of said jaws is formed with a notch for receiving said curved needle and preventing said needle from being displaced laterally of said jaws.

3. The suturing machine of claim 2, wherein another of said jaws is provided with a stop positioned opposite to said notch and adapted to prevent said curved needle from being displaced vertically of said jaws.

4. A suturing machine for use in medical treatment by producing continuous stitches on parts to be sutured, comprising a curved needle for holding a needle thread; means for holding said needle and operative for inserting said curved needle into the parts to be sutured to form a thread loop; a shuttle for holding a shuttle thread; means for holding said shuttle and operative for inserting the shuttle thread into said thread loop to thereby interlock said loop and to produce a lock stitch, said shuttle holding means being mounted on said needle holding means and being operative when said needle holding means is inoperative with said needle in the raised position, said needle holding means including an elongated frame formed with a grip, and a needle supporting bar connected to said frame and holding said curved needle, said frame beinf formed with a guiding bore, said shuttle holding means including a support rod and a shuttle holder connected thereto, said support rod being guided in said guiding bore of said elongated frame to be displaced lengthwise thereof for moving said shuttle holder towards and from the thread loop formed by said curved needle.

5. The suturing machine of claim 4, wherein said shuttle holder includes a housing formed with a chamber to receive said shuttle, a holding element for supporting the shuttle in said chamber and formed with a fork-like end portion, and a spring acting on said holding element to press said end portion against said shuttle, said shuttle holder being formed with a clearance for the thread loop to pass therethrough.

* * * * *